United States Patent [19]
Dryden

[11] Patent Number: 5,284,160
[45] Date of Patent: Feb. 8, 1994

[54] CONSOLIDATED ANESTHESIA CIRCUIT

[76] Inventor: Gale E. Dryden, 5835 N. Tacoma, Indianapolis, Ind. 46220

[21] Appl. No.: 791,289

[22] Filed: Nov. 13, 1991

[51] Int. Cl.⁵ ............................................. A61M 15/00
[52] U.S. Cl. ........................... 128/203.12; 128/205.12; 128/911
[58] Field of Search ............ 128/203.12, 204.18, 128/205.12, 911, 719, 912, 909

[56] References Cited

U.S. PATENT DOCUMENTS

| | | | |
|---|---|---|---|
| 3,856,051 | 12/1974 | Bain | 128/203.12 |
| 4,007,737 | 2/1977 | Paluch | 128/201.13 |
| 4,265,235 | 5/1981 | Fukunaga | 128/200.24 |
| 4,320,754 | 3/1982 | Watson et al. | 128/911 |
| 4,446,869 | 5/1984 | Knodle | 128/716 |
| 4,463,755 | 8/1984 | Suzuki | 128/204.18 |
| 4,621,634 | 11/1986 | Nowacki et al. | 128/204.18 |
| 4,637,384 | 1/1987 | Schroeder | 128/204.18 |
| 4,676,239 | 6/1987 | Humphrey | 128/911 |
| 4,677,987 | 7/1987 | Choksi | 128/719 |
| 4,717,403 | 1/1988 | Choksi | 128/205.27 |
| 4,723,543 | 2/1988 | Beran | 128/207.14 |
| 4,838,258 | 6/1989 | Dryden et al. | 128/204.18 |
| 4,852,563 | 8/1989 | Gross | 128/202.27 |
| 4,852,564 | 8/1989 | Sheridan et al. | 128/204.18 |
| 4,924,860 | 5/1990 | Larsen et al. | 128/205.12 |
| 4,967,744 | 11/1990 | Chua | 128/204.18 |
| 4,991,576 | 2/1991 | Henkin et al. | 128/203.28 |

*Primary Examiner*—Edgar S. Burr
*Assistant Examiner*—Aaron J. Lewis
*Attorney, Agent, or Firm*—Woodard, Emhardt, Naughton, Moriarty & McNett

[57] ABSTRACT

A sampling adaptor suitable for use in a unilimb breathing system with three or more hoses that includes a breathing hose connector, a swivel to allow the breathing hose connector to rotate freely in relation to the remainder of the adaptor, an angular swivel to allow adjustment of the angular shape of the adaptor, a filter that encloses the sampling end of a flexible sampling hose, a patient end connector, is disclosed herein.

18 Claims, 5 Drawing Sheets

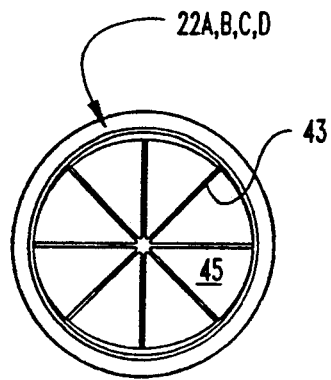
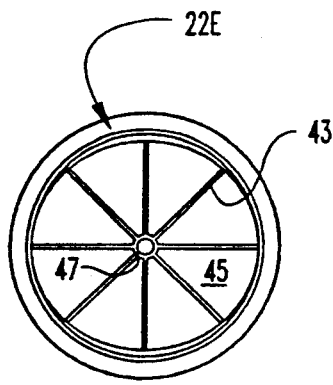
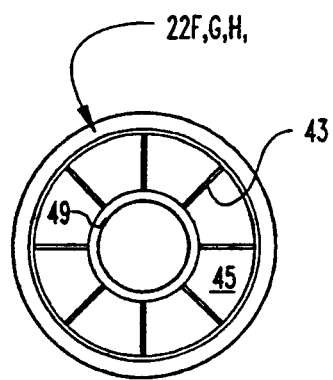
Fig.2　　　Fig.3　　　Fig.4
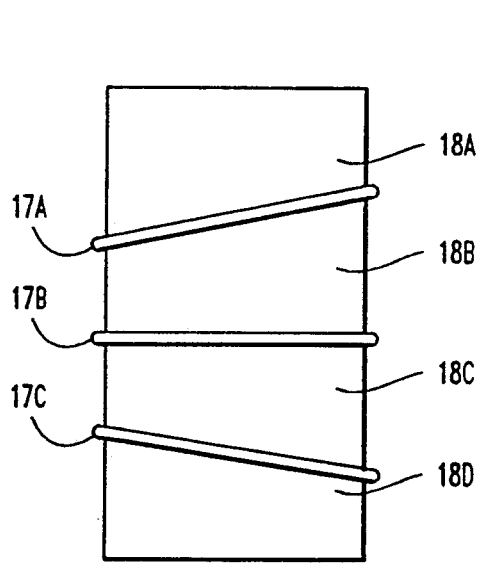
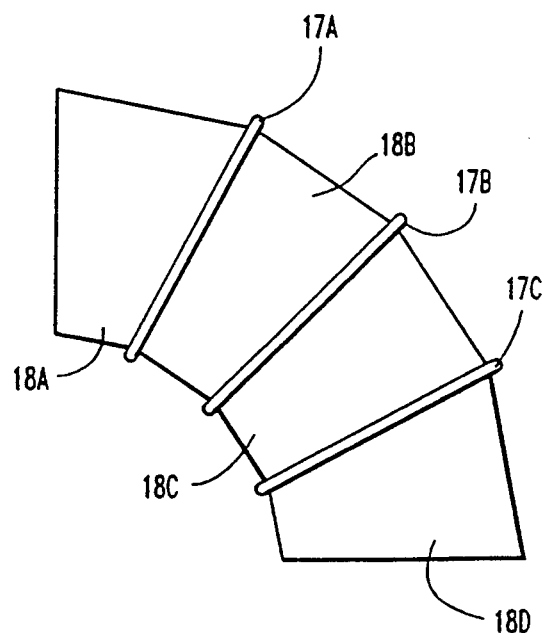
Fig.5　　　Fig.6

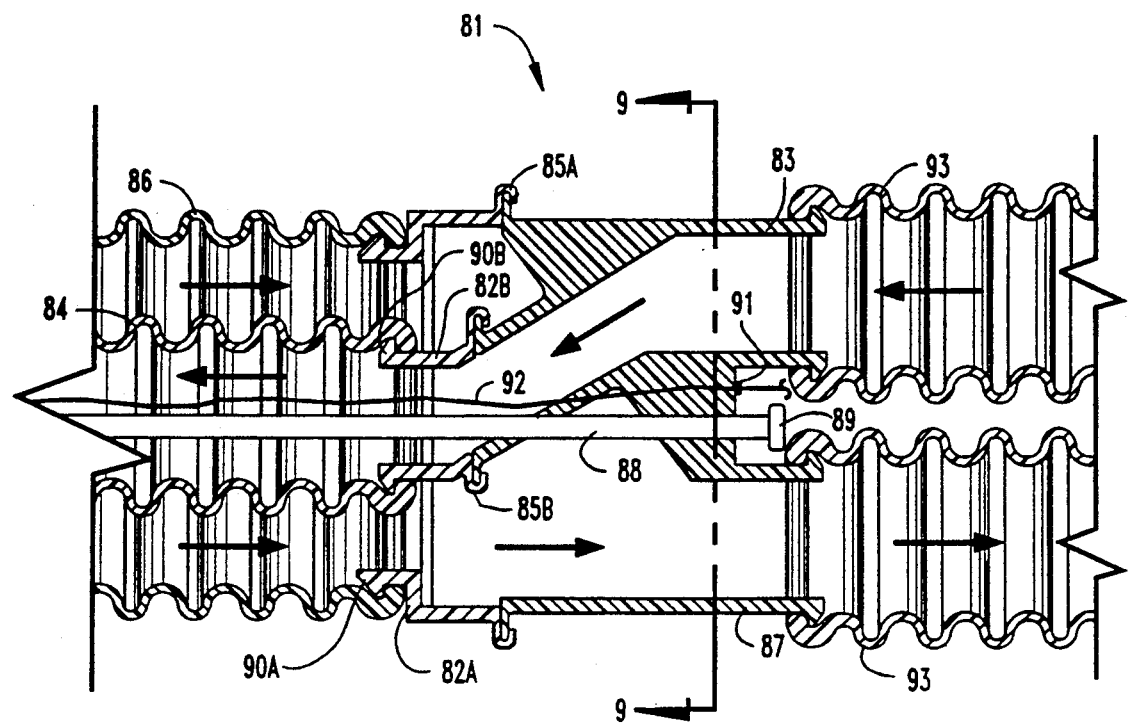
Fig. 8
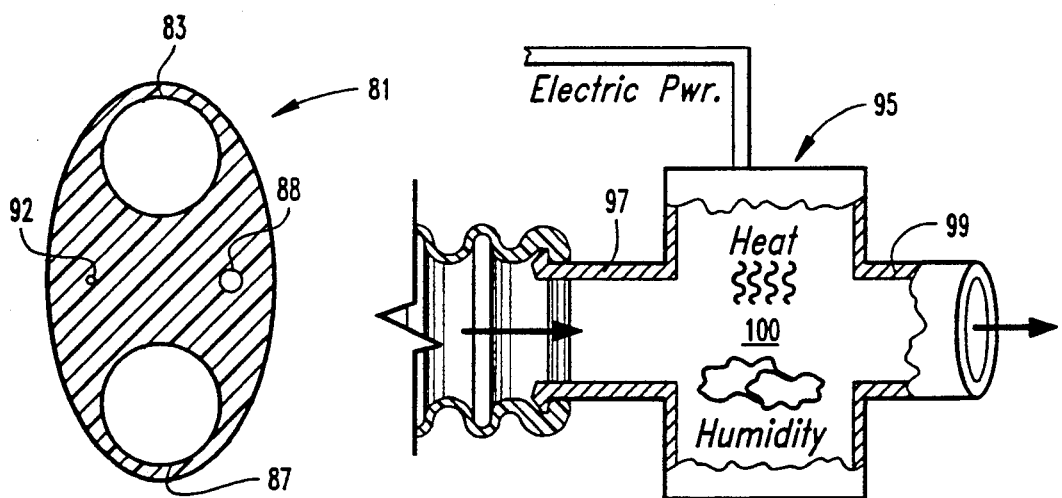
Fig. 9
Fig. 10

CONSOLIDATED ANESTHESIA CIRCUIT

FIELD OF INVENTION

This invention relates to unilimb breathing circuits and more particularly to unilimb breathing circuits with provisions for sampling gases while filtering and separating the sample from fluid condensate.

BACKGROUND

The sampling of expired gases from breathing circuits in anesthesia is a well-known practice. It is desirable that the sample be taken as closely as possible to the patient's mouth piece. This helps to minimize mixing of the exhaled gases with inspired gases. It is also desirable to minimize the number of hoses that run from the patient to the respiratory machine. A reduction in the number of hoses that run to the patient, produces a corresponding reduction in the likelihood of having hoses become tangled or obstructed by torquing of the hoses.

U.S. Pat. No. 3,856,051 to Bane discloses a double lumen unilimb device where the inspired and expired air are contained within one limb that has an inner and outer hose. This design reduces the number of external hoses between the patient and the machinery from three tubes to two tubes if a sampling line is utilized and from four tubes to three tubes if a temperature probe or heater is also utilized. A unilimb design for respiratory hoses lowers heat loss to the patient. The reduction of heat loss occurs due to heat transfer between the exhaled and inhaled gases through the walls of the hoses in the unilimb. The unilimb design also reduces heat loss from heated inspired air because of the shielding by the warm outer expiratory tube.

U.S. Pat. No. 4,838,258 to Dryden et al. discloses a hose arrangement that includes a sampling hose contained inside one of two single lumen respiratory hoses. The other respiratory hose runs to the respirator as a single hose.

While the prior art has utilized double lumen unilimb hoses, several single-lumen hoses are still required with such unilimb hoses. Therefore, there remains a need to further reduce the number of lines between the patient and machine and to reduce the possibility of tangling and torquing of the breathing hoses. This may be accomplished according to my invention by providing a unilimb device that carries all of the required hoses or lines to the patient, the inspiratory gas hose, the expiratory gas hose, the sampling hose and any other required hoses or lines.

It is well-known that water vapor condensate interferes with analysis of gas samples that are taken from gas sampling hoses. The problem is created by the cooling of the moist exhaled gases from the patient, which causes water vapor to condense. Various types of water traps have been utilized to reduce the amount of condensate that reaches the gas analyzers. U.S. Pat. No. 4,717,403 to Choksi is an example of liquid traps utilized to prevent liquid condensation collection in gas analyzers. This device uses a separation chamber to separate the gas from the liquid. A liquid trap is an additional device to be placed in line prior to the gas analyzer to provide protection if an analyzer is to be utilized. Many liquid traps are not fully effective in preventing condensation from reaching gas analyzers. Provision must also be made for the emptying of condensate, for the trap to retain its effectiveness.

The patient on a respirator loses water as well as heat. I have determined that a device able to transfer the humidity from the expired air to the inspired air would reduce this moisture loss and decrease the problem of condensation from exhaled gases. The inspired air would also require less moisture to be added prior to inhalation by the patient and, therefore, less processing. A combination heat and humidity exchange device present in the patient end of the respiratory apparatus would be ideal for the patient and healthcare professional. Such a device that is able to separate gases from liquid condensate, and that also functions to exchange heat and moisture from expired air to the inspired air, and which is also part of the gas sampling device, is needed due to distinct advantages in terms of efficiency and simplicity of use. Such a device would reduce the need to heat and humidify inspired air and reduce the problems of handling collected condensates from the expired gas.

Mucus plugs are commonly encountered in respiratory devices, and frequently clog smaller hoses such as gas sampling hoses. These mucus plugs must be removed from the hose in order to obtain readings of gas composition from the sampling hose. I believe it is desirable to protect the sampling hose by preventing mucus from reaching it and thereby reduce the problems of mucus clogged hoses.

It would also be helpful to have a temperature sensor to measure the temperature of inspired gases after heat transfer from exhaled gases in the unilimb hose and heat transfer from the heat and moisture exchange media, to determine the degree of warming required for the inspired gases. The temperature may be determined by the use of a temperature probe in the region where the inhaled and exhaled gases mix.

Special connectors are desirable to incorporate my improvements and to allow compatibility with standard 15 and 22 mm respiratory connectors. Hoses for a unilimb breathing system may become twisted by torquing of the hose between the patient and machine. Therefore swivels which allow the remainder of the device to remain stationary while the hose connectors are free to rotate are helpful in order to eliminate torquing and to retain unobstructed airways. U.S. Pat. No. 4,967,744 to Chua utilizes one swivel in a swivel patient connector. While a single swivel allows rotation of the patient breathing device (mask, endotracheal tube) relative to the patient connector, the flexible breathing hose may still undergo torquing and may become obstructed unless, and according to one feature of my invention, at least one swivel and preferably two swivels are located in the patient adaptor (patient connector), one at each end, and at least one swivel is located on the machine end adaptor. These additional swivels according to my invention allow each end of the flexible breathing hose to rotate. The flexible breathing hose may rotate at the patient breathing device, the sampling adaptor or at the machine adaptor to prevent hose torquing.

In patient treatment, utilizing a breathing system, it is often necessary to vary the orientation of the patient end of the adaptor based on the relative position of the patient and the breathing means. In some instances, a 90° elbow may be required between the adaptor and the breathing means (patient breathing mask or endotracheal tube), and in other instances, a straight connection is required. A patient end adaptor that is variable from a straight orientation to that of a 90° bend is an improvement that I have incorporated to optimize the patient end adaptor orientation for each patient's use and to simplify installation of the apparatus because extra elbows or adaptors are no longer required.

SUMMARY OF THE INVENTION

One aspect of the present invention relates to a sampling adaptor for use with a breathing system that includes breathing hose connections, swivels to allow the breathing hose connector to rotate in relation to the remainder of the adaptor, an angular swivel or angular swivels to allow adjustment of the angular shape of the adaptor, a filter that encloses the sampling end of a flexible sampling hose to enable particulate and liquid contaminants to be removed from the sampled gases, and means to connect the adaptor to a breathing mask, endotracheal tube or similar type devices.

It is an object of the present invention to provide a sampling tube adaptor for use with unilimb tubing that conveys the inspiratory gas to the patient, and the expiratory gas and sampled gas to the appropriate machine.

It is a another object of the present invention to inhibit solid and liquid contaminants from reaching the sampling tube.

It is a further object of the present invention to provide a sampling adaptor with means to allow adjustment to provide optimal orientation for patient usage.

It is another object of the present invention to enable use with conventional respiratory apparatus.

It is a further object of the invention to allow use of the invention with closed or semi-closed rebreathing systems or with non-rebreathing systems.

BRIEF DESCRIPTION OF THE DRAWINGS

FIGS. 2, 3 and 4 are frontal views of the apertured supports illustrating the apertures which allow unrestricted flow of gases.

FIGS. 5 and 6 are elevational sectional views of the angular swivel with a straight orientation in FIG. 5 and adjusted to form a 90° elbow in FIG. 6.

FIG. 8 is a longitudinal sectional view of an alternate embodiment of the machine adaptor that allows the use of standard single lumen connectors.

FIG. 9 is a cross sectional view of the adaptor in FIG. 8.

FIG. 10 is a schematic diagram of an external chamber for the addition of heat and humidity.

DESCRIPTION OF THE PREFERRED EMBODIMENT

Figure 1:
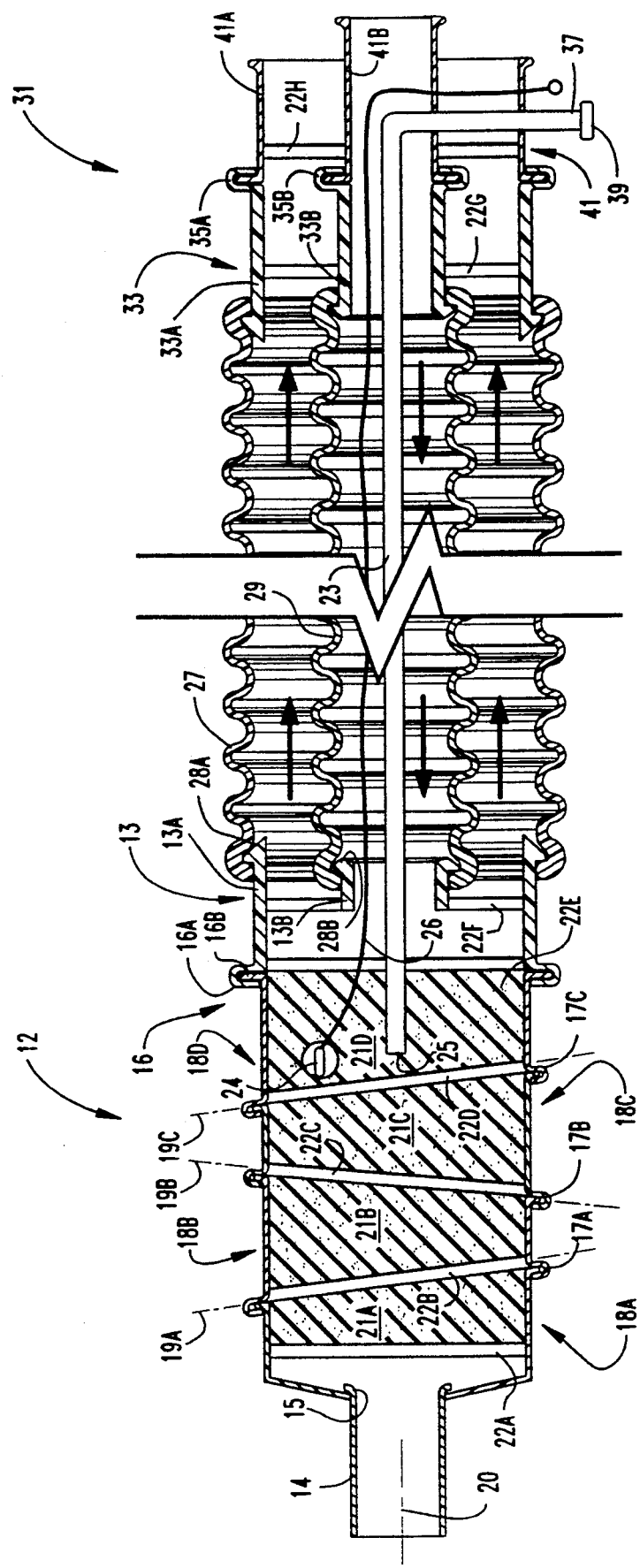
FIG. 1 is a longitudinal sectional view of one embodiment of the present invention where an internal sampling tube is used and the patient end of the sampling tube is surrounded by a filter, and an angular swivel is provided to allow adjustment of the angular shape of the adaptor, and swivels are provided that allow the breathing hose connectors to rotate in relation to fixed adaptor ends.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

The present invention includes a unilimb breathing assembly that contains at least three hoses. The unilimb contains an outer expiratory hose, an inner inspiratory hose and a sampling hose. The present invention also includes heat and humidity exchange media, swivels to help reduce torquing of the unilimb, a filtered sampling hose and also includes an angular swivel to vary the angular relationship of the sampling adaptor to the patient breathing device. The patient breathing device may be a mask or an endotracheal tube.

Referring now to FIG. 1, a sampling adaptor 12 is illustrated that has a breathing hose connector 13 having an outer breathing hose connector 13A with a lip 28A and an inner breathing hose connector 13B with a lip 28B, a patient end connector 14, a patient end hose swivel 15, a breathing hose connector swivel 16, with a breathing hose connector section 16A and a main body section 16B. The sampling adaptor also has three angular rotatable swivels 17A, 17B, and 17C that connect four relatively rotatable sections 18A, 18B, 18C and 18D defined by the angular swivels. This rotation allows a sampling adaptor conformation that is straight as in FIG. 5 or that may be varied by a 180° rotation of the several sections around the swivels to provide a 90° elbow as in FIG. 6.

This embodiment of the invention also has filters in four sections, filters 21A, 21B, 21C and 21D. Filter 21A is contained in the section 18A, 21B is in section 18B, 21C is in section 18C and 21D is in section 18D. Filter 21A is contained by apertured supports 22A and 22B (See FIGS. 1 and 2). Apertured support 22A acts as a screen to prevent the movement of filter 21A into the patient end connector, and apertured support 22E prevents filter 21D from moving past the main body portion of the angular swivel. Apertured supports 22B and 22C also help retain the filters in the appropriate sections.

The sampling adaptor 12 also contains a sampling hose 23 that runs from the sampling adaptor to the machine adaptor 31 and is provided with sufficient length to avoid sampling hose tension which might otherwise be caused by the stretching of the flexible breathing hoses. This can be done by arranging the sampling hose 23 as was done for tube 21 in Dryden et al. U.S. Pat. No. 4,838,258, discussed above. The patient end 25 of the sampling hose 23 is contained within filter 21D and is held in the center of the sampling adaptor on center line 20 by the apertured support 22E (See FIG. 3). An apertured support 22F (See FIG. 4) connects the inner breathing hose connector 13B with the outer breathing hose connector 13A.

A temperature sensing probe 24 is enclosed by filter 21D. A wire 26 runs from the probe to exit at the machine adaptor 31. The temperature probe is located in the filter material where the heat and humidity exchange occurs to provide data about the temperature of inspired gases. This data may be used to control an external heat and humidity exchange chamber 95 (See FIG. 10) to optimize the heat and humidity of the inspired gas.

The flexible outer breathing hose 27 is utilized to conduct expired gases from the sampling adaptor 12 to the machine adaptor 31 and the flexible inner breathing hose 29 is used to convey inspiratory gases from the machine adaptor 31 to the sampling adaptor 12. The flexible outer breathing hose 27 and the flexible inner breathing hose 29 are connected to the machine end adaptor 31 by the breathing hose connector 33. The outer breathing hose connector 33A connects the outer breathing hose 27 and the inner breathing hose connector 33B connects the inner breathing hose 29.

The machine end adaptor 31 also has an outer swivel 35A and an inner swivel 35B. The machine end adaptor 31 has an apertured support 22G which is fixed to and supports the inner 33B and outer 33A hose connectors. Apertured support 22H is fixed to and supports outer and inner connectors 41A and 41B, respectively, of the machine end connector 41. The sampling hose is connected to a sampling port 37 that includes a Luer Lock connector 39. The port 37 is fixed to connector 41A and 41B by a solvent seal. The Luer Lock connector allows the attachment of a Luer Lock line to any currently used gas analyzers in order to analyze the patient expired gases.

This invention is adaptable to a closed or semi-closed absorption system, if the absorber has function directional valves and active soda lime. The invention is also adaptable as a non-rebreathing circuit when the inspiratory hose is connected to a fresh gas flow from the gas machine and the expiratory gas hose is attached to an out-flow system that includes the overflow control valve, breathing bag, and scavenge system by means of a tee adaptor that fits a 22 mm. bag nipple.

The flexible breathing hoses 27 and 29 that are attached to the sampling adaptor 12 may be coaxial (See FIG. 1) or they may run separately. The flexible breathing hoses may be connected to the breathing hose connectors and/or the Luer Lock ports by use of a solvent seal (as shown with the sampling port 37) or by friction fit over an expanded lip (as shown by outer flexible breathing hose 27 fitted over lip 28A). The flexible breathing hoses may be with or without reinforcing corrugated spiral ridges. The filters 21A, 21B, 21C and 21D utilized in this embodiment of the invention, may be composed of a fibrous material or polymeric foam having a comparatively large surface area that is capable of filtering out dust size particles and mucus plugs and is suitable for separating liquid condensates from gaseous compositions.

The sampling hose may be run in either the inner flexible breathing hose (as shown) or between the inner and outer flexible breathing hose. If the sampling hose is run between the inner and outer flexible breathing hoses, the sampled gas will be warmed by the expired gases and will have less condensation from the cooling of the sample. If it is preferred to allow condensation to occur prior to the exit of the sampling hose from the unilimb, the sampling hose may be run in the inner flexible hose where the inspired gases may cool the sampled gas more quickly to achieve greater extraction of moisture from the sampled gas.

An inventive method for use of the device described in FIG. 1 is performed by attaching the machine end adaptor portion 31 to a respirator gas input and output, by attaching the sampling port to a gas analyzer by Luer Lock compatible connectors, by attaching the sampling adaptor to a patient gas mask or endotracheal tube, by adjusting the angular swivel to provide optimum orientation of the sampling adaptor for use by the patient, by filtering the gas sample of expired gases through the filter prior to analysis by the gas analyzer to remove solid and liquid contaminants, by analyzing the expired gases and the gas analyzer and by adjusting the composition of inspired gases to provide optimal composition for the patient as determined by the analysis of the expired gases.

FIGS. 2, 3 and 4 illustrate the apertured supports 22. The hoses and connectors are not shown, to simplify the figures. FIG. 2 illustrates apertured supports 22A, 22B, 22C and 22D and the basic structure of the apertured supports which are comprised of spokes 43 and apertures 45 between the spokes. FIG. 3 illustrates the apertured support 22E which has spokes 43, apertures 45 and a sampling hose support 47 that surrounds and retains the sampling hose in place. FIG. 4 illustrates apertured supports 22F, 22G and 22H which have spokes 43, apertures 45 and inner hose support 49 that supports the inner hose connector assembly within the outer hose connector assembly to which the outer section of the spokes are attached.

FIG. 5 and 6 illustrate two conformations of the sampling adaptor. FIGS. 5 and 6 illustrate the result of rotation of sections 18A, 18B, 18C and 18D about the angular swivels 17A, 17B and 17C which allow an unlimited range of configuration of the sampling adaptor from straight (FIG. 5) to a 90° bend (FIG. 6).

Figure 7:
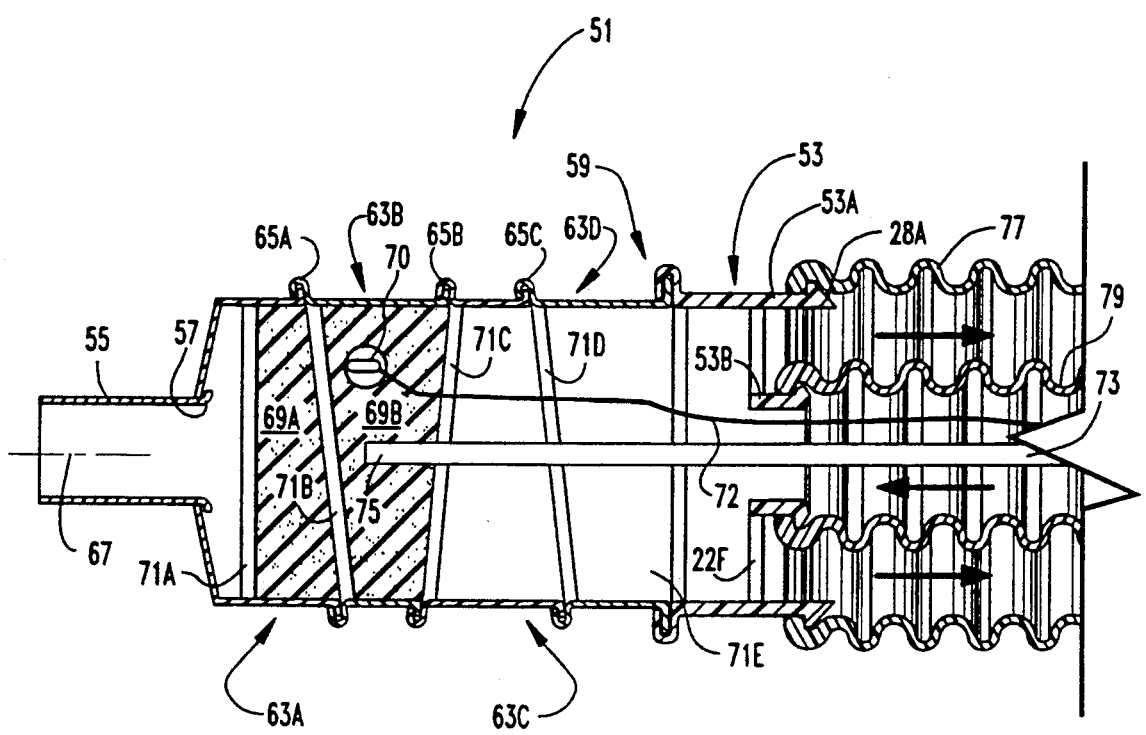
FIG. 7 is a longitudinal sectional view of an alternate embodiment of the sampling adaptor.

FIG. 7 illustrates an alternative embodiment of the sampling adaptor. Sampling adaptor 51 has a breathing hose connector 53 comprised of an outer breathing hose connector 53A and an inner breathing hose connector 53B. The breathing hose connector 53 is attached to a breathing hose swivel 59. A patient end connector 55 is attached to a patient end swivel 57. Angular swivels 65A, 65B and 65C allow rotation of patient end sections 63A, 63B, 63C and 63D about the angular swivels. In this embodiment, the sampling adaptor contains a filter in sections 63A and 63B. Filter 69A is retained between apertured support 71A and apertured support 71B and is located in section 63A. Filter 69B is located in section 63B and is retained between apertured support 71B and 71C.

A sampling hose 73 passes from filter 69B toward the breathing hose connector 53 and is supported in the center of apertured support 71C and 71D. The sampling hose 73, in this embodiment, is supported and retained by the apertured support as described in previous figures. The patient end 75 of the sampling hose 73 is centered in filter 69B and is surrounded by filter material on all sides to ensure filtration of all sampled gas. A temperature sensing probe 70 is enclosed by filter 69B. A wire 72 runs from the probe toward the machine adaptor where it exits the hose. The outer flexible breathing hose 77 is connected to the outer breathing hose connector 53A and the inner flexible breathing hose 79 is connected to the inner breathing hose connector 53B.

Referring to FIG. 8, an alternate embodiment of a machine end adaptor 81 is illustrated which has an outer swivel 85A and an inner swivel 85B. Machine end adaptor 81 adapts the multi-line unilimb by connectors for the attachment of standard single lumen hoses. For example, machine end adaptor 81 has a inspiratory gas connector 83 and exhaled gas connector 87 that are compatible with standard connectors and which allows connection of a standard 22 mm breathing hose 93 thereto. In this illustration, the inner flexible breathing hose 84 is connected to the inner breathing hose connector 82B by a lip 90B. In this embodiment, the inspiratory gases flow from the inspiratory gas connector 83 to the inner flexible breathing hose 84. The outer flexible breathing hose 86 is connected to the outer breathing hose connector 82A by a lip 90A. Exhaled gases flow from the outer flexible breathing hose 86 to the exhaled gas connector 87. The sampling hose 88 which runs to a sampling hose port 89 is attached by a solvent seal to adaptor 81, and the wire 92 for the temperature probe to a terminal 91 for the temperature probe.

FIG. 9 is a cross-sectional view of the machine end adaptor 81. This view illustrates the inspiratory gas connector 83, the exhaled gas connector 87, the sampling hose 88 and the wire 92 for temperature probe 70 (in FIG. 7).

FIG. 10 illustrates an external heat and humidity adding chamber. Based upon the requirements of the patient, the inspiratory gases from the respirator may be run into the chamber 95 for addition of heat and humidity which consists of an input adaptor 97 and an output adaptor 99 and a chamber to provide heat and humidity 100. As depicted, water for a humidifier and electric power for a heater are supplied to the chamber. Dry cool gases enter and warm moist gases leave the external heat and humidity adding chamber. This device may be controlled by a servo mechanism and a temperature probe in the sampling adaptor.

The filters present in the sampling adaptors of FIGS. 1 and 7 serve to filter and separate gases from liquid condensate, and enable condensation from exhaled gases to evaporate and hydrate the relatively drier inspired air. The filters function to exchange humidity from the expired gas to the inspired gas due to their relatively large surface area. As a large surface area buffer between respirations, the filters also act to exchange heat between the expired gases and the inspired gases. Thus, the filters also act as humidity and heat exchange media, as well as, serve to filter the sampled gases to prevent clogging of the sampling hose.

The inventive method of delivering a variable mixture of gases for patient inhalation requires the inventive devices, a respiratory machine, patient breathing means, which may be a mask or endotracheal tube, gas analyzer and may require several standard respiratory hoses depending upon the set up. The respiratory machine is attached to the machine end adaptor and the sampling port is attached to the gas analyzer. The sampling adaptor is attached to the patient breathing means, and the angular swivels on the sampling adaptor are adjusted for optimal conformation relative to the patient breathing means and the sampling adaptor.

Figure 11:
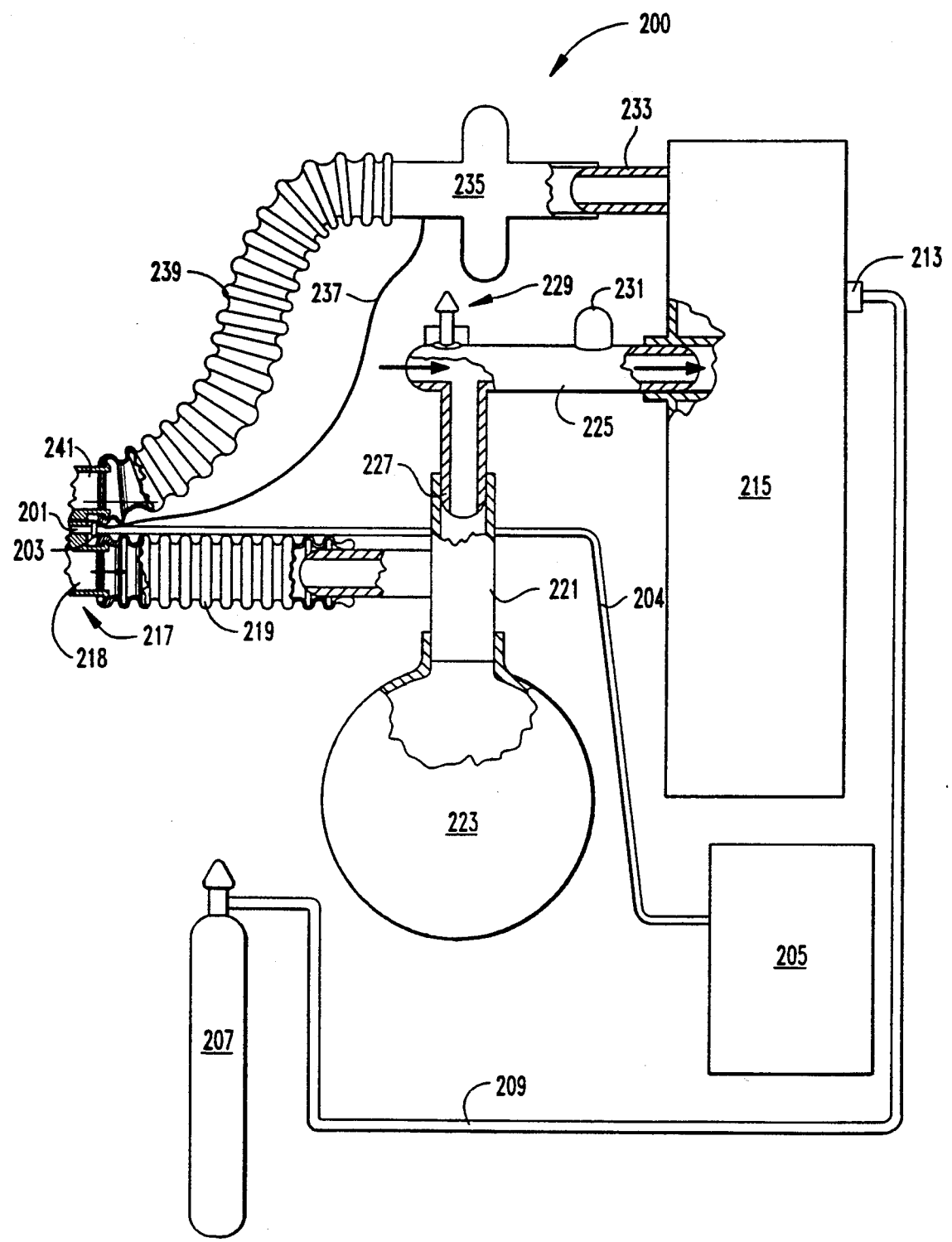
FIG. 11 illustrates a consolidated anesthesia circuit according to the present invention.

As shown in FIG. 11, the consolidated anesthesia circuit may be utilized as a closed or semi-closed absorption system or may be utilized as a non-rebreathing circuit. The non-rebreathing circuit may be set up by connecting the inspiratory gas hose to a fresh gas flow from the gas machine and attaching the expiratory gas hose to an out-flow system that includes the over flow control valve, breathing bag and scavenge system by means of a tee adaptor that fits a 22 mm bag nipple.

Referring further to FIG. 11, a consolidated anesthesia circuit 200 is shown. A gas sample from the patient is filtered through the filter (not shown) prior to analysis to remove solid and liquid contaminants. The sampled gas passes through the sampling hose 201 through the sampling port 203 through a second sampling hose 204 to the gas analyzer 205. The patient gases are analyzed and the composition of the inspiratory gases is adjusted to provide optimal composition for the patient as determined by the analyzer. A gas cylinder 207 contains gas for addition to the consolidated anesthesia circuit 200. A gas output line 209 runs from the gas cylinder 207 to a carbon dioxide absorber inlet port 213 of a conventional gas machine 215. In the present embodiment, the gas flow is adjusted by the anesthesiologist manually adjusting valves in the gas machine, based upon the gas readings from the analyzer. In other embodiments, the amount of fresh gas may be adjusted by valves at a separate location.

In the present embodiment, by having the gas output line 209 run through the carbon dioxide absorber inlet port 213, fresh gas can be warmed and moistened by the soda lime in the carbon dioxide absorber of the gas machine 215. The carbon dioxide absorber is utilized in a closed or semi-closed rebreathing system, but is unnecessary in non-rebreathing systems. In the system as shown, expired gases leave the exhaled gas connector 218 of the machine end adaptor 217 via an expiratory hose 219. The expiratory hose 219 runs to a tee connector 221 to which a breathing bag 223 is attached. The tee is attached to an input arm 225 of the carbon dioxide absorber in the gas machine. The input arm also has an adjustable overflow valve 229 and a scavenge port 231.

An inspiratory limb 233 on the carbon dioxide absorber in gas machine 215 allows gases to pass from the machine into the heat and humidity adding chamber 235 (see FIG. 10). An electrically conductive wire 237 runs from a temperature probe such as 24 in FIG. 1 or 70 in FIG. 7 in the sampling adaptor, into a control unit at the heat and humidity adding chamber 235. The amount of heat and humidity may be varied according to the temperature of the gases at the probe. The inspiratory hose 239 runs from the heat and humidity adding chamber to the inspiratory gas connector 241 on the machine end adaptor 217.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A unilimb breathing assembly comprising:
   a flexible outer breathing hose suitable to pass patient expiratory gas and having a patient end and a machine end;
   a flexible inner breathing hose suitable to pass patient inspiratory gas and having a patient end and a machine end, said inner breathing hose being contained within said outer flexible breathing hose;
   a flexible sampling hose suitable to convey sampled gas to an analyzer, and having a sampling end and a machine end and contained within at least one of said flexible outer and inner breathing hoses for the majority of the length of said sampling hose;
   a sampling adaptor with a breathing hose connector connected to said breathing hoses, a swivel to allow said breathing hose connector to rotate freely in relation to the remainder of the adaptor, an angular swivel to allow adjustment of the angular shape of the adaptor, a filter which encloses said sampling end of said sampling hose, and a patient end connector means; and
   a machine end adaptor having a hose end and a machine end and, at the hose end, having a breathing hose connector secured to said outer and inner flexible breathing hoses, the machine end adaptor having a sampling port connected to said machine end of said sampling hose, and having a machine input connector communicating with said outer breathing hose, and a machine output connector communicating with said inner breathing hose.

2. The assembly of claim 1 wherein said sampling hose is contained within said flexible inner breathing hose for the majority of the length of said sampling hose.

3. The assembly of claim 1 further comprising an internal heater and an access line to said internal heater, and said access line is contained between said flexible outer and inner breathing hose.

4. The assembly of claim 1 further comprising a temperature probe and an access line to said temperature probe, and said access line is contained between said flexible outer and inner breathing hose.

5. The assembly of claim 1 wherein said sampling port includes a Luer Lock port, and said machine end of said sampling hose includes a hose sealed and anchored at said Luer Lock port and extending through said patient end of said outer and inner flexible breathing hose into said filter.

6. The assembly of claim 1 wherein said outer and inner flexible breathing hoses are secured to said breathing hose connectors by a solvent seal.

7. The assembly of claim 1 wherein said outer and inner flexible breathing hoses are secured to said breathing hose connectors by a friction fit.

8. The assembly of claim 1 wherein said breathing hose connector is suitable for attachment of a unilimb breathing hose thereto.

9. The assembly of claim 1 wherein said breathing hose connector is suitable for attachment of a plurality of single lumen breathing hoses.

10. The assembly of claim 1 wherein said swivel allows 360 degree rotation of the breathing hose connectors about the sampling adaptor connected thereto.

11. The assembly of claim 10 wherein said sampling hose is centered in and secured to an apertured support in said sampling adaptor and said apertured support allows unrestricted flow of gases.

12. The assembly of claim 1 wherein said filter is divided into at least two sections by said angular swivel, and each section of said filter is contained by said apertured supports within a section connected to said angular swivel, and each filter section rotates as said section containing said filter rotates.

13. The assembly of claim 12 further comprising a plurality of angular swivels and said angular swivels connect a plurality of sections and said angular swivels provide a variable orientation of said sampling adaptor from a relatively straight adaptor to an adaptor with a 90 degree bend by a 180 degree rotation of the sections.

14. The assembly of claim 1 wherein said filter is comprised of a fibrous material of comparatively large surface area suitable for filtering out dust sized particles, filtering mucus, separating liquid condensates from gaseous compositions, facilitation of evaporation of condensates into inspired air and providing for an exchange of a portion of the heat from the expired air to the inspired air.

15. The assembly of claim 14 wherein said filter is comprised of a polymeric foam material of comparatively large surface area.

16. A method of delivering a variable mixture of gases for patient inhalation comprising the steps of:
providing the assembly of claim 1; a respiratory machine, a patient breathing means and a gas analyzer;
attaching said machine end adaptor portion to a gas input and a gas output of said respiratory machine;
attaching said sampling port to said gas analyzer;
attaching said sampling adaptor to a patient breathing means;
adjusting the angular swivel on said sampling adaptor for optimal conformation relative to said patient breathing means;
filtering a gas sample through said filter, prior to analysis by said gas analyzer, to remove solid and liquid contaminates;
analyzing the filtered expired patient gases by said analyzer; and
adjusting the composition of the inspired gases to provide optimal composition for the patient as determined by said analysis of said sampled expired gases by said gas analyzer.

17. The method of claim 16 wherein said patient breathing means is a patient mask.

18. The method of claim 16 wherein said patient breathing means is an endotracheal tube.

* * * * *